US008017758B2

(12) United States Patent
Stender et al.

(10) Patent No.: US 8,017,758 B2
(45) Date of Patent: Sep. 13, 2011

(54) **PNA OLIGOMERS, OLIGOMER SETS, METHODS AND KITS PERTAINING TO THE DETECTION OF *BACILLUS ANTHRACIS***

(75) Inventors: Henrik Stender, Gentofte (DK); Jens J. Hyldig-Nielsen, Holliston, MA (US)

(73) Assignee: Boston Probes, Inc., Bedford, MA (US)

( * ) Notice: Subject to any disclaimer, the term of this patent is extended or adjusted under 35 U.S.C. 154(b) by 2377 days.

(21) Appl. No.: 10/393,855

(22) Filed: Mar. 21, 2003

(65) Prior Publication Data

US 2003/0232402 A1 Dec. 18, 2003

Related U.S. Application Data

(60) Provisional application No. 60/366,424, filed on Mar. 21, 2002.

(51) Int. Cl.
*C07H 21/04* (2006.01)
*A61K 31/70* (2006.01)
*C12Q 1/68* (2006.01)

(52) U.S. Cl. ............................. 536/24.5; 514/44; 435/6

(58) Field of Classification Search .................. None
See application file for complete search history.

(56) References Cited

U.S. PATENT DOCUMENTS

| | | | | |
|---|---|---|---|---|
| 5,527,675 A | * | 6/1996 | Coull et al. | 435/6 |
| 5,539,082 A | * | 7/1996 | Nielsen et al. | 530/300 |
| 5,612,458 A | * | 3/1997 | Hyldig-Nielsen et al. | 530/388 |
| 5,623,049 A | * | 4/1997 | Löbberding et al. | 530/300 |
| 5,714,331 A | * | 2/1998 | Buchardt et al. | 435/6 |
| 5,719,262 A | * | 2/1998 | Buchardt et al. | 530/300 |
| 5,736,336 A | * | 4/1998 | Buchardt et al. | 435/6 |
| 5,766,855 A | * | 6/1998 | Buchardt et al. | 435/6 |
| 5,773,571 A | * | 6/1998 | Nielsen et al. | 530/300 |
| 5,786,461 A | * | 7/1998 | Buchardt et al. | 536/18.7 |
| 5,837,459 A | * | 11/1998 | Berg et al. | 435/6 |
| 5,891,625 A | * | 4/1999 | Buchardt et al. | 435/6 |
| 5,948,680 A | * | 9/1999 | Baker et al. | 435/375 |
| 5,972,610 A | * | 10/1999 | Buchardt et al. | 435/6 |
| 5,986,053 A | * | 11/1999 | Ecker et al. | 435/6 |
| 6,027,893 A | * | 2/2000 | Ørum et al. | 435/6 |
| 6,107,470 A | * | 8/2000 | Nielsen et al. | 536/23.1 |
| 6,110,676 A | * | 8/2000 | Coull et al. | 435/6 |
| 6,201,103 B1 | * | 3/2001 | Nielsen et al. | 530/300 |
| 6,228,982 B1 | * | 5/2001 | Norden et al. | 530/300 |
| 6,280,964 B1 | * | 8/2001 | Kavanaugh et al. | 435/7.8 |
| 6,287,772 B1 | * | 9/2001 | Stefano et al. | 435/6 |
| 6,355,421 B1 | * | 3/2002 | Coull et al. | 435/6 |
| 6,357,163 B1 | * | 3/2002 | Buchardt et al. | 43/6 |
| 6,361,942 B1 | * | 3/2002 | Coull et al. | 435/6 |
| 6,441,152 B1 | * | 8/2002 | Johansen et al. | 536/23.1 |
| 6,448,016 B1 | | 9/2002 | Rastogi et al. | 435/6 |
| 6,475,721 B2 | * | 11/2002 | Kleiber et al. | 435/6 |
| 6,485,901 B1 | * | 11/2002 | Gildea et al. | 435/5 |
| 6,569,630 B1 | | 5/2003 | Vivekananda et al. | 435/6 |

FOREIGN PATENT DOCUMENTS

| | | | |
|---|---|---|---|
| WO | WO92/20702 | * | 11/1992 |
| WO | WO92/20703 | * | 11/1992 |
| WO | WO96/27680 | * | 9/1996 |
| WO | WO97/12995 | | 4/1997 |
| WO | WO99/21881 | * | 5/1999 |
| WO | WO99/22018 | * | 5/1999 |
| WO | WO99/37670 | * | 7/1999 |
| WO | WO99/49293 | * | 9/1999 |
| WO | WO02/57493 | * | 7/2002 |

OTHER PUBLICATIONS

Alignment of SEQ ID No. 1 with sequence of US 6605709, result 4 of .rni database, STIC sequence search of Jan. 13, 2006.*
Altmann, K., et al, "Polyamide Based Nucleic Acid Analogs—Synthesis of d-Amino Acids With Nucleic Acid Bases Bearing Side Chains". Bioorganic& Medicinal Chemistry Letters, 7, 1119-1122 (1997).*
Petersen, K. et al, "Synthesis and Oligomerization of N°-Noc-N°-(thymine-1-ylacetyl)omithine". Bioorganic & Medicinal Chemistry Letters, 6, 793-796 (1996).
Seela, et al, Nucl. Acids, Res., 28, 3224-3232 (2000).
Tomac, S. et al, "Ionic Effects on the Stability and Conformation of Peptide Nucleic Acid Complexes". J. Am. Chem. Soc., 118, 5544-5552 (1996).
Weiler, J. et al,"Hybridisation Based DNA Screening on Peptide Nucleic Acid (PNA) Oligomer Arrays". Nucl. Acids Res., 25, 2792-2799 (1997).
Yaron, et al, Analytical Biochemistry, 95, 228-235 (1979).
Castro et al, "Ultrasensitive, direct detection of a specific DNA sequence of *Bacillus anthracis* in solution", Analyst, 2000, vol. 125, pp. 9-11.
Qi, et al, "Utilization of the rpoB Gene as a Specific Chromosomal Marker for Real-Time PCR Detection of *Bacillus anthracis*", Applied and Environmental Microbiology, Aug. 2001, vol. 67, No. 8, p. 3720-3727.
Ph.d. Thesis by Jesper Lohse, Faculty of Science, University of Copenhagen, "The Principle of Non-Complementarity" (1997).
Tyagi, S. et al., "Molecular Beacons: Probes that Fluoresce upon Hybridization", Nature Biotechnology, vol. 14, pp. 303-308, Mar. 1996.
Ash, et al, FEMS Mier bi 1 gy Letters, 94, 75-80 (1992).
Bergman, F. et al, "Solid Phase Synthesis of Directly Linked PNA-DNA Hybrids". Tett. Lett., 36, 6823-6826 (1995).
Cantin, M. et al, "Synthesis of the Monomeric Building Blocks of Z-Olefinic PNA (Z-OPA) Containing the Bases Adenine and Thymine". Tett. Lett., 38, 4211-4214 (1997). Ciapetti, P. et al, "Synthesis of N-Fmoc-a-Amino Acids Carrying the Four DNA Nucleobases in the Side Chain". Tetrahedron, 53, 1167-1176 (1997).
Diderichsen, U. et al, "Alanyl-PNA Oligomers: A New System for Identification". Bioorganic & Med. Chem. Lett., 7, 1743-1746 (1997).
Diderichsen, U. et al, "Alanyl-PNA Homoduplex: A-T Pairig With the N7-Regioisomer of Adenine". Bioorganic & Med. Chem. Lett., 8, 165-168 (1998).
Diderichsen, U. et al, "Self-Pairing PNA With Alternating Alanyl/Homoalanyl Backbone". Tett. Lett., 37, 475-478 (1996).
Egholm, M. et al, "PNA Hybridizes to Complementary Oligonucleotides Obeying the Watson-Crick Hydrogen-Bonding Rules". Nature, 365, 566-568 (1998).

(Continued)

Primary Examiner — Tracy Vivlemore

(57) ABSTRACT

This invention is related to novel PNA probes, probe sets, methods and kits pertaining to the determination of *Bacillus anthracis*.

27 Claims, 1 Drawing Sheet
(1 of 1 Drawing Sheet(s) Filed in Color)

OTHER PUBLICATIONS

Fiandaca, M. et al, "PNA Blocker Probes Enhance Specificity in Probe Assays". Peptide Nucleic Acids: Protocols and Applications, p. 129-141, 1999.

Fujii, M. et al, "Nucleic Acid Analog Peptide (NAAP) 2. Synthesis and Properties of Novel DNA Analog Peptides Containing Nucleobase Linked β-Aminoalanine". Bioorg. Med. Chem. Lett.. 7, 637-627 (1997).

Gildea, B. et al, "PNA Solubility Enhancers". Tett. Lett., 39, 7255-7258 (1988).

Good, L. et al, "Review Progress in Developing PNA As a Gene-Targeted Drug". Antisense & Nucleic Acid Drug Development, 7, 431-437 (1997).

Guo, Z. et al, "Enhanced Discrimination of Single Nucleotide Polymorphisms by Artificial Mismatch Hybridization". Nature Biotechnology, 15, 331-335 (1997).

Haaima, G. et al, "Peptide Nucleic Acids (PNAs) Containing Thymine Monomers Derived From Chiral Amino Acids: Hybridization and Solubility Properties of D-Lysine PNA". Angew. Chem Int. Ed. Engl, 35, 1939-1942, 1996.

Howarth, N. et al, "a-PNA: A Novel Peptide Nucleic Acid Analogue of DNA". J. Org. Chem, 62, 5441-5450 (1997).

Jordan, S. et al, "New Hetero-Oligomeric Peptide Nucleic Acids With Improved Binding Properties to Complementary DNA". Bioorg. Med. Chem. Lett., 7, 687-690 (1997).

Krotz, A. et al, "Synthesis of 'Retro-Inverso' Peptide Nucleic Acids: 2. Oligomerization and Stability". Tett. Lett., 36, 6941-6944 (1995).

Kumar, V. et al, "Pyrrolidine Nucleic Acids: DNA/PNA Oligomers With 2-Hydroxy/Aminomethyl- 4-(thymin-1-yl) Pyrrolidine-N-Acetic Acid". Organic Letters, 3 (9), 1269-1272 (2001).

Lagriffoul, P.et al, "The Synthesis, Co-Oligomerization and Hybridization of a Thymine-Thymine Heterodimer Containing PNA". Bioorganic & Medicinal Chemistry Letters, 4, 1081-1082 (1994).

Lagriffoul, P. et al, "Peptide Nucleic Acids With a Conformationally Constrained Chiral Cyclohexyl-Derived Backbone". Chem. Eur. J., 3, 912-919 (1997).

Lester, A. et al, PNA Array Technology, at Biochip Technologies Conference, Annapolis (Oct. 1997).

Lesnik, E. et al, "Triplex Formation Between DNA and Mixed Purine-Pyrimidine PNA Analog With *Lysines* in Backbone". Nucleosides & Nucleotides, 16, 1775-1779 (1997).

Lohse, J. et al, "Double Duplex Invasion by Peptide Nucleic Acid: A General Principle for Sequence-Specific Targeting of Double-Stranded DNA". PNAS, 96 (21) 11804-11808 (1999).

Lowe, G. et al, "Amino Acids Bearing Nucleobases for the Synthesis of Novel Peptide Nucleic Acids". J. Chem. Soc. Perkin Trans., 1, 539-546 (1997).

Lowe, G. et al, "Dipeptides Bearing Nucleobases for the Synthesis of Novel Peptide Nucleic Acids". J. Chem. Soc. Perkin Trans., 11, 547-554 (1997).

Lowe, G. et al, "Solid-Phase Synthesis of Novel Peptide Nucleic Acids". J. Chem. Soc. Perkin Trans., 11, 555-560 (1997).

Nielsen, P. et al, "Peptide Nucleic Acids (PNAs): Potential Anti-sense and Anti-gene Agents". Anti-Cancer Drug Design, 8, 53-65 (1993).

* cited by examiner

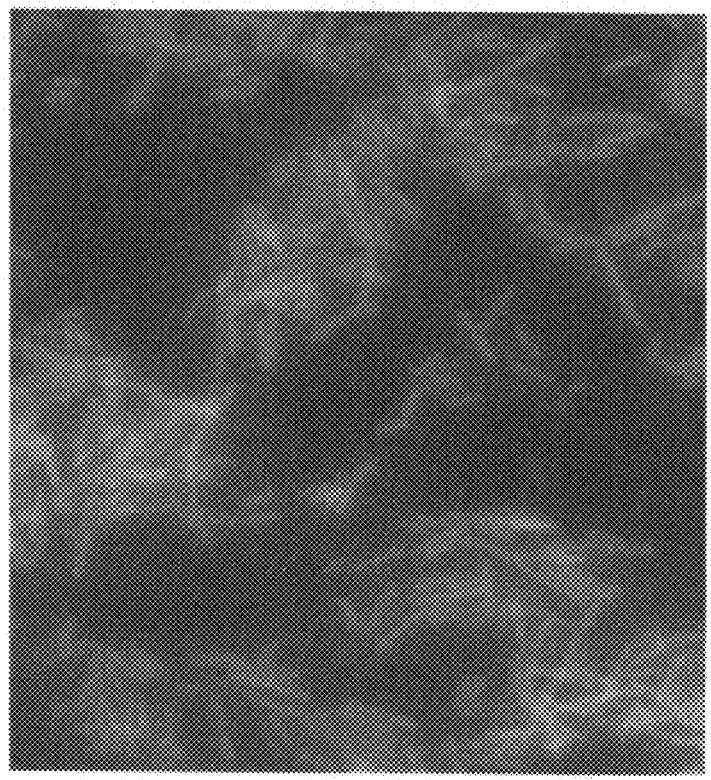
Figure 1A
Figure 1B

SEQUENCE LISTING

<160> NUMBER OF SEQ ID NOS: 3

<210> SEQ ID NO 1
<211> LENGTH: 15
<212> TYPE: DNA
<213> ORGANISM: Artificial Sequence
<220> FEATURE:
<223> OTHER INFORMATION: Description of Combined DNA/RNA Molecule: PNA
      Probe Sequence
<220> FEATURE:
<223> OTHER INFORMATION: Description of Artificial Sequence:PNA Probe
      Sequence

<400> SEQUENCE: 1
ccassggtat cddtc                                                     15

<210> SEQ ID NO 2
<211> LENGTH: 15
<212> TYPE: DNA
<213> ORGANISM: Artificial Sequence
<220> FEATURE:
<223> OTHER INFORMATION: Description of Combined DNA/RNA Molecule:PNA
      Probe Sequence
<220> FEATURE:
<223> OTHER INFORMATION: Description of Artificial Sequence:PNA Probe
      Sequence

<400> SEQUENCE: 2
ttcaaaggct cccgc                                                     15

<210> SEQ ID NO 3
<211> LENGTH: 15
<212> TYPE: DNA
<213> ORGANISM: Artificial Sequence
<220> FEATURE:
<223> OTHER INFORMATION: Description of Combined DNA/RNA Molecule:PNA
      Probe Sequence
<220> FEATURE:
<223> OTHER INFORMATION: Description of Artificial Sequence:PNA Probe
      Sequence

<400> SEQUENCE: 3
ttcaatggct cccgc                                                     15

PNA OLIGOMERS, OLIGOMER SETS, METHODS AND KITS PERTAINING TO THE DETECTION OF *BACILLUS ANTHRACIS*

CROSS REFERENCE TO RELATED APPLICATIONS

This application claims the benefit of U.S. Provisional Application No. 60/366,424 filed on Mar. 21, 2002.

BACKGROUND OF THE INVENTION

1. Field of the Invention

This invention is related to the field of probe-based detection, analysis and/or quantitation of microorganisms. More specifically, this invention relates to novel PNA oligomers, oligomer sets, methods and kits pertaining for the detection, identification and/or enumeration of *Bacillus anthracis*.

2. Introduction

Nucleic acid hybridization is a fundamental process in molecular biology. Probe-based assays are useful in the detection, quantitation and/or analysis of nucleic acids. Nucleic acid probes have long been used to analyze samples for the presence of nucleic acid from bacteria, fungi, virus or other organisms and are also useful in examining genetically based disease states or clinical conditions of interest. Nonetheless, probe-based assays have been slow to achieve commercial success. This lack of commercial success is, at least partially, the result of difficulties associated with specificity, sensitivity and reliability.

Despite its name, peptide nucleic acid (PNA) is neither a peptide, a nucleic acid nor is it an acid. PNA is a non-naturally occurring polyamide that can hybridize to nucleic acid (DNA and RNA) with sequence specificity (See: U.S. Pat. No. 5,539,082 and Egholm et al., *Nature* 365: 566-568 (1993)). Being a non-naturally occurring molecule, unmodified PNA is not known to be a substrate for the enzymes that are known to degrade peptides or nucleic acids. Therefore, PNA should be stable in biological samples, as well as have a long shelf life. Unlike nucleic acid hybridization, which is very dependent on ionic strength, the hybridization of a PNA with a nucleic acid is fairly independent of ionic strength and is favored at low ionic strength, conditions that strongly disfavor the hybridization of nucleic acid to nucleic acid (Egholm et al., *Nature*, at p. 567). The effect of ionic strength on the stability and conformation of PNA complexes has been extensively investigated (Tomac et al., *J. Am. Chem. Soc.* 118:55 44-5552 (1996)). Sequence discrimination is more efficient for PNA recognizing DNA than for DNA recognizing DNA (Egholm et al., *Nature*, at p. 566). However, the advantages in point mutation discrimination with PNA probes, as compared with DNA probes, in a hybridization assay, appears to be somewhat sequence dependent (Nielsen et al., *Anti-Cancer Drug Design* 8:53-65, (1993) and Weiler et al., *Nucl. Acids Res.* 25: 2792-2799 (1997)).

Though they hybridize to nucleic acid with sequence specificity (See: Egholm et al., *Nature*, at p. 567), PNAs have been slow to achieve commercial success at least partially due to cost, sequence specific properties/problems associated with solubility and self-aggregation (See: Bergman, F., Bannwarth, W. and Tam, S., *Tett. Lett.* 36:6823-6826 (1995), Haaima, G., Lohse, A., Buchardt, O. and Nielsen, P. E., *Angew. Chem. Int. Ed. Engl.* 35:1939-1942 (1996) and Lesnik, E., Hassman, F., Barbeau, J., Teng, K. and Weiler, K., *Nucleosides & Nucleotides* 16:1775-1779 (1997) at p 433, col. 1, ln. 28 through col. 2, ln. 3) as well as the uncertainty pertaining to non-specific interactions that might occur in complex systems such as a cell (See: Good, L. et al., *Antisense & Nucleic Acid Drug Development* 7:431-437 (1997)). However, problems associated with solubility and self-aggregation may have been reduced or eliminated (See: Gildea et al., *Tett. Lett.* 39: 7255-7258 (1998)). Nevertheless, because of their unique properties, PNA is clearly not the equivalent of a nucleic acid in either structure or function. Consequently, PNA probes should be evaluated for performance and optimization to thereby confirm whether they can be used to specifically and reliably detect a particular nucleic acid target sequence, particularly when the target sequence exists in a complex sample such as a cell, tissue or organism.

SUMMARY OF THE INVENTION

This invention is directed to PNA oligomers, oligomer sets, methods and kits useful for detecting, identifying and/or quantitating (enumerating) *Bacillus anthracis*, or the rRNA or rDNA associated therewith, in a sample.

Thus, in one embodiment, this invention pertains to PNA oligomers. The PNA oligomers of this invention can comprise a probing nucleobase sequence, wherein at least a portion of the probing nucleobase sequence is at least ninety percent homologous to the nucleobase sequences, or their complements, selected from the group consisting of: CCA-SSG-GTA-TCD-DTC (Seq. ID No. 1) and TTC-AAA-GGC-TCC-CGC (Seq. ID No. 2). The PNA oligomers may comprise one or more non-natural nucleobases so that the oligomers do not substantially intra or inter molecularly self-hybridize. The PNA oligomers may be capable of sequence-specifically hybridizing to a target sequence within the nucleic acid of *Bacillus anthracis*, or the rRNA or rDNA associated therewith. It is to be understood that the foregoing characteristics are not mutually exclusive.

In another embodiment, this invention pertains to PNA oligomer sets. For example, an oligomer set may comprise two or more oligomers, at least one of which is a PNA oligomer comprising a probing nucleobase sequence that is at least ninety percent homologous to the nucleobase sequences, or their complements, selected from the group consisting of: CCA-SSG-GTA-TCD-DTC (Seq. ID No. 1) and TTC-AAA-GGC-TCC-CGC (Seq. ID No. 2). The oligomer sets may be a set comprising two or more PNA oligomers, at least one of which may comprise one or more non-natural nucleobases so that the oligomers do not substantially intra or inter molecularly self-hybridize. The PNA oligomers may be capable of sequence-specifically hybridizing to a target sequence within the nucleic acid of *Bacillus anthracis*, or the rRNA or rDNA associated therewith. It is to be understood that the foregoing characteristics are not mutually exclusive.

In yet another embodiment, this invention pertains to methods for determining *Bacillus anthracis*, or the rRNA or rDNA associated therewith in a sample. Determining the nucleic acid of *Bacillus anthracis* can be used to detect, identify and/or quantitate (enumerate) *Bacillus anthracis* spores or organisms. For example, the method can comprise contacting a sample, under suitable hybridization conditions, with at least one PNA oligomer that is capable of sequence-specifically hybridizing to a target sequence within the rRNA of *Bacillus anthracis*. The PNA oligomer may comprise may comprise one or more non-natural nucleobases so that the PNA oligomer does not substantially intra or inter molecularly self-hybridize. According to the method, hybridization of the probing nucleobase sequence to the target sequence may be detected, identified and/or quantitated. Because hybridization requires sequence specific complex formation between the target sequence and the PNA oligomer, the result can be correlated with the presence, absence and/or quantity of *Bacillus anthracis* in the sample. This correlation is possible because determination of the formation of the complex can be used to determine the presence, absence and/or quantity of *Bacillus anthracis* in a sample.

In yet another embodiment, the method for determining the *Bacillus anthracis* can comprise contacting a sample, under suitable hybridization conditions, with at least one PNA oligomer comprising a probing nucleobase sequence that is at least ninety percent homologous to the nucleobase sequences, or their complements, selected from the group consisting of: CCA-SSG-GTA-TCD-DTC (Seq. ID No. 1) and TTC-AAA-GGC-TCC-CGC (Seq. ID No. 2). Sequence specific hybridization of the probing nucleobase sequence of a PNA oligomer to a target sequence within the nucleic acid of *Bacillus anthracis*, or the rRNA or rDNA associated therewith, can be detected, identified and/or quantitated. Because hybridization requires sequence specific complex formation between the target sequence and the PNA oligomer, the result can be correlated with the presence, absence and/or quantity of *Bacillus anthracis*, or the rRNA or rDNA associated therewith, in the sample.

In still another embodiment, this invention pertains to kits for determining the *Bacillus anthracis*, or the rRNA or rDNA associated therewith, in a sample and/or the presence, absence and/or number of *Bacillus anthracis* organisms and/or spores in a sample. The kit can comprise one or more PNA oligomers. At least one of the PNA oligomers can comprise a probing nucleobase sequence that is at least ninety percent homologous to the nucleobase sequences, or their complements, selected from the group consisting of: CCA-SSG-GTA-TCD-DTC (Seq. ID No. 1), TTC-AAA-GGC-TCC-CGC (Seq. ID No. 2) and TTC-AAT-GGC-TCC-CGC (Seq. ID No. 3). The kit can also comprise other reagents, instructions and/or compositions necessary to perform the assay. In another embodiment, the kit may comprise a PNA oligomer that comprises one or more non-natural nucleobases so that the PNA oligomers do not substantially intra or inter molecularly self-hybridize.

Since *Bacillus anthracis* can be a biowarfare pathogen, the PNA oligomers, oligomer sets, methods and/or kits of this invention may be useful for the determination of *Bacillus anthracis* in air, food, beverages, water, pharmaceutical products, personal care products, dairy products, environmental samples, mail and/or packaging as well as in equipment used to process, store and/or handle any of the foregoing. Additionally, the PNA oligomers, oligomer sets, methods and/or kits of this invention may be useful for the determination of *Bacillus anthracis* in clinical samples and/or clinical environments. By way of a non-limiting example, the PNA oligomers, oligomer sets, methods and/or kits of this invention may be useful in the analysis of culture samples, or subcultures thereof. Other non-limiting examples of clinical samples include, but are not limited to: sputum, laryngeal swabs, gastric lavage, bronchial washings, biopsies, aspirates, expectorates, body fluids (e.g. spinal, pleural, pericardial, synovial, blood, pus, amniotic, and urine), bone marrow and/or tissue sections, or cultures or subcultures thereof. The PNA oligomers, oligomer sets, methods and/or kits may also be useful for the analysis of clinical specimens, equipment, fixtures and/or products used to treat humans and/or animals. Assays used to perform analysis for *Bacillus anthracis* include, for example, in-situ assays and/or assays wherein nucleic acid amplification (e.g. PCR) is performed.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1A and FIG. 1B are color images of *B. anthracis* (1A) and *B. pseudomycoides* (1B) analyzed by fluorescence in situ hybridization using Bant23S02/Flu. Organisms of *B. anthracis* are identified by the fluorescein-labeled PNA probe and thus appear bright green fluorescent in FIG. 1A, whereas organisms of *B. pseudomycoides* in FIG. 1B appear faint red.

DISCUSSION OF THE INVENTION

1. Definitions a. As used herein, "nucleobase" means those naturally occurring and those non-naturally occurring heterocyclic moieties commonly known to those who utilize nucleic acid technology or utilize peptide nucleic acid technology to thereby generate polymers that can sequence specifically bind to nucleic acids. Non-limiting examples of suitable nucleobases include, but are not limited to: adenine, cytosine, guanine, thymine, uracil, 5-propynyl-uracil, 2-thio-5-propynyl-uracil, 5-methylcytosine, pseudoisocytosine, 2-thiouracil and 2-thiothymine, 2-aminopurine, N9-(2-amino-6-chloropurine), N9-(2,6-diaminopurine), hypoxanthine, N9-(7-deaza-guanine), N9-(7-deaza-8-aza-guanine) and N8-(7-deaza-8-aza-adenine). Other non-limiting examples of suitable nucleobase include those nucleobases illustrated in FIGS. 2(A) and 2(B) of Buchardt et al. (U.S. Pat. No. 6,357,163 or WO92/20702 or WO92/20703), herein incorporated by reference).

b. As used herein, "nucleobase sequence" means any segment, or aggregate of two or more segments, of a polymer, that comprises nucleobase-containing subunits. Non-limiting examples of suitable polymers include oligodeoxynucleotides (e.g. DNA), oligoribonucleotides (e.g. RNA), peptide nucleic acids (PNA), PNA chimeras, PNA oligomers, nucleic acid analogs and/or nucleic acid mimics.

c. As used herein, "target sequence" is a nucleobase sequence of a polynucleobase strand sought to be determined. The target sequence can be a subsequence of the rRNA of *Bacillus anthracis*.

d. As used herein, "polynucleobase strand" means a complete single polymer strand comprising nucleobase-containing subunits. An example of a polynucleobase strand is a single nucleic acid strand.

e. As used herein, "nucleic acid" is a nucleobase sequence-containing polymer, or polymer segment, having a backbone formed from nucleotides, or analogs thereof. Preferred nucleic acids are DNA and RNA. For the avoidance of any doubt, PNA is a nucleic acid mimic and not a nucleic acid or nucleic acid analog.

f. As used herein, "peptide nucleic acid" or "PNA" means any oligomer or polymer segment comprising two or more PNA subunits (residues), including, but not limited to, any of the oligomer or polymer segments referred to or claimed as peptide nucleic acids in U.S. Pat. Nos. 5,539,082, 5,527,675, 5,623,049, 5,714,331, 5,718,262, 5,736,336, 5,773,571, 5,766,855, 5,786,461, 5,837,459, 5,891,625, 5,972,610, 5,986,053 and 6,107,470; all of which are herein incorporated by reference. The term "peptide nucleic acid" or "PNA" shall also apply to any oligomer or polymer segment comprising two or more subunits of those nucleic acid mimics described in the following publications: Lagriffoul et al., *Bioorganic & Medicinal Chemistry Letters*, 4: 1081-1082 (1994); Petersen et al., *Bioorganic & Medicinal Chemistry Letters*, 6: 793-796 (1996); Diderichsen et al., *Tett. Lett.* 37: 475-478 (1996); Fujii et al., *Bioorg. Med. Chem. Lett.* 7: 637-627 (1997);

Jordan et al., *Bioorg. Med. Chem. Lett.* 7: 687-690 (1997); Krotz et al., *Tett. Lett.* 36: 6941-6944 (1995); Lagriffoul et al., *Bioorg. Med. Chem. Lett.* 4: 1081-1082 (1994); Diederichsen, U., *Bioorganic & Medicinal Chemistry Letters*, 7: 1743-1746 (1997); Lowe et al., *J. Chem. Soc. Perkin Trans.* 1, (1997) 1: 539-546; Lowe et al., *J. Chem. Soc. Perkin Trans.* 11: 547-554 (1997); Lowe et al., *J. Chem. Soc. Perkin Trans.* 1 1:5 55-560 (1997); Howarth et al., *J. Org. Chem.* 62: 5441-5450 (1997); Altmann, K-H et al., *Bioorganic & Medicinal Chemistry Letters*, 7: 1119-1122 (1997); Diederichsen, U., *Bioorganic & Med. Chem. Lett.*, 8: 165-168 (1998); Diederichsen et al., *Angew. Chem. Int. Ed.*, 37: 302-305 (1998); Cantin et al., *Tett. Lett.*, 38: 4211-4214 (1997); Ciapetti et al., *Tetrahedron*, 53: 1167-1176 (1997); Lagriffoule et al., *Chem. Eur. J.*, 3: 912-919 (1997); Kumar et al., *Organic Letters* 3(9): 1269-1272 (2001); and the Peptide-Based Nucleic Acid Mimics (PENAMs) of Shah et al. as disclosed in WO96/04000.

In certain embodiments, a "peptide nucleic acid" or "PNA" is an oligomer or polymer segment comprising two or more covalently linked subunits of the formula:

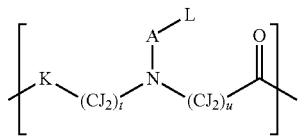

wherein, each J is the same or different and is selected from the group consisting of H, $R^1$, $OR^1$, $SR^1$, $NHR^1$, $NR^1_2$, F, Cl, Br and I. Each K is the same or different and is selected from the group consisting of O, S, NH and $NR^1$. Each $R^1$ is the same or different and is an alkyl group having one to five carbon atoms that may optionally contain a heteroatom or a substituted or unsubstituted aryl group. Each A is selected from the group consisting of a single bond, a group of the formula; $-(CJ_2)_s-$ and a group of the formula; $-(CJ_2)_sC(O)-$, wherein, J is defined above and each s is a whole number from one to five. Each t is 1 or 2 and each u is 1 or 2. Each L is the same or different and is independently selected from: adenine, cytosine, guanine, thymine, uracil, 5-propynyl-uracil, 2-thio-5-propynyl-uracil, 5-methylcytosine, pseudoisocytosine, 2-thiouracil and 2-thiothymine, 2-aminopurine, N9-(2-amino-6-chloropurine), N9-(2,6-diaminopurine), hypoxanthine, N9-(7-deaza-guanine), N9-(7-deaza-8-aza-guanine) and N8-(7-deaza-8-aza-adenine), other naturally occurring nucleobase analogs or other non-naturally occurring nucleobases.

In certain other embodiments, a PNA subunit consists of a naturally occurring or non-naturally occurring nucleobase attached to the N-α-glycine nitrogen of the N-[2-(aminoethyl)]glycine backbone through a methylene carbonyl linkage; this currently being the most commonly used form of a peptide nucleic acid subunit.

f. As used herein, the terms "label" and "detectable moiety" shall be interchangeable and refer to moieties that can be attached to a nucleobase polymer (e.g. PNA probe), antibody or antibody fragment to thereby render the nucleobase polymer, antibody or antibody fragment detectable by an instrument or method.

g. As used herein, "sequence specifically" means hybridization by base pairing through hydrogen bonding. Non-limiting examples of standard base pairing includes adenine base pairing with thymine or uracil and guanine base pairing with cytosine. Other non-limiting examples of base-pairing motifs include, but are not limited to: adenine base pairing with any of: 5-propynyl-uracil, 2-thio-5-propynyl-uracil, 2-thiouracil or 2-thiothymine; guanine base pairing with any of: 5-methylcytosine or pseudoisocytosine; cytosine base pairing with any of: hypoxanthine, N9-(7-deaza-guanine) or N9-(7-deaza-8-aza-guanine); thymine or uracil base pairing with any of: N9-(2-aminopurine), N9-(2-amino-6-chloropurine) or N9-(2,6-diaminopurine) [sometimes identified herein using the one letter code "D"]; 2-thiouridine and 2-thiothymidine base pairing with N9-(2,6-diaminopurine), and N8-(7-deaza-8-aza-adenine), being a universal base, base pairing with any other nucleobase, such as for example any of: adenine, cytosine, guanine, thymine, uracil, 5-propynyl-uracil, 2-thio-5-propynyl-uracil, 5-methylcytosine, pseudoisocytosine, 2-thiouracil [sometimes identified herein using the one letter code "S"] and 2-thiothymine, 2-aminopurine, N9-(2-amino-6-chloropurine), N9-(2,6-diaminopurine), hypoxanthine, N9-(7-deaza-guanine) or N9-(7-deaza-8-aza-guanine) (See: Seela et al., *Nucl. Acids, Res.*: 28(17): 3224-3232 (2000)).

h. As used herein, "quenching" means a decrease in fluorescence of a fluorescent reporter moiety caused by energy transfer associated with a quencher moiety, regardless of the mechanism of quenching.

i. As used herein "solid support" or "solid carrier" means any solid phase material upon which an oligomer is synthesized, attached, ligated or otherwise immobilized. Solid support encompasses terms such as "resin", "solid phase", "surface" and "support". A solid support may be composed of organic polymers such as polystyrene, polyethylene, polypropylene, polyfluoroethylene, polyethyleneoxy, and polyacrylamide, as well as co-polymers and grafts thereof. A solid support may also be inorganic, such as glass, silica, controlled-pore-glass (CPG), or reverse-phase silica. The configuration of a solid support may be in the form of beads, spheres, particles, granules, a gel, or a surface. Surfaces may be planar, substantially planar, or non-planar. Solid supports may be porous or non-porous, and may have swelling or non-swelling characteristics. A solid support may be configured in the form of a well, depression or other container, vessel, feature or location. A plurality of solid supports may be configured in an array at various locations, addressable for robotic delivery of reagents, or by detection means including scanning by laser illumination and confocal or deflective light gathering.

j. As used herein, "support bound" means immobilized on or to a solid support. It is understood that immobilization can occur by any means, including for example; by covalent attachment, by electrostatic immobilization, by attachment through a ligand/ligand interaction, by contact or by depositing on the surface.

k. "Array" or "microarray" means a predetermined spatial arrangement of oligomers present on a solid support or in an arrangement of vessels. Certain array formats are referred to as a "chip" or "biochip" (M. Schena, Ed. *Microarray Biochip Technology*, BioTechnique Books, Eaton Publishing, Natick, Mass. (2000). An array can comprise a low-density number of addressable locations, e.g. 2 to about 12, medium-density, e.g. about a hundred or more locations, or a high-density number, e.g. a thousand or more. Typically, the array format is a geometrically regular shape that allows for fabrication, handling, placement, stacking, reagent introduction, detection, and/or storage. The array may be configured in a row and column format, with regular spacing between each location. Alternatively, the locations may be bundled, mixed or homogeneously blended for equalized treatment or sampling. An array may comprise a plurality of addressable locations configured so that each location is spatially addressable for high-throughput handling, robotic delivery, masking, or sampling of reagents, or by detection means including scanning by laser illumination and confocal or deflective light gathering.

2. Description

I. Generally Applicable Subject Matter:
PNA Synthesis:

Methods for the chemical assembly of PNAs are well known (See: U.S. Pat. Nos. 5,539,082, 5,527,675, 5,623,049, 5,714,331, 5,718,262, 5,736,336, 5,773,571, 5,766,855, 5,786,461, 5,837,459, 5,891,625, 5,972,610, 5,986,053, 6,107,470, 6,201,103, 6,228,982 and 6,357,163; all of which are herein incorporated by reference (Also see: PerSeptive Biosystems Product Literature)). As a general reference for PNA synthesis methodology also please see: Nielsen et al., *Peptide Nucleic Acids; Protocols and Applications*, Horizon Scientific Press, Norfolk England (1999).

Chemicals and instrumentation for the support bound automated chemical assembly of peptide nucleic acids are now commercially available. Both labeled and unlabeled PNA oligomers are likewise available from commercial vendors of custom PNA oligomers. Chemical assembly of a PNA is analogous to solid phase peptide synthesis, wherein at each cycle of assembly the oligomer possesses a reactive alkyl amino terminus that is condensed with the next synthon to be added to the growing polymer.

PNA may be synthesized at any scale, from submicromole to millimole, or more. PNA can be conveniently synthesized at the 2 μmole scale, using Fmoc(Bhoc) protecting group monomers on an Expedite Synthesizer (Applied Biosystems) using a XAL, PAL or many other commercially available peptide synthesis supports. Alternatively, the Model 433A Synthesizer (Applied Biosystems) with a suitable solid support (e.g. MBHA support) can be used. Moreover, many other automated synthesizers and synthesis supports can be utilized. Synthesis can be performed using continuous flow method and/or a batch method. PNA can be manually synthesized.

Regardless of the synthetic method used, because standard peptide chemistry is utilized, natural and non-natural amino acids can be routinely incorporated into a PNA oligomer. Because a PNA is a polyamide, it has a C-terminus (carboxyl terminus) and an N-terminus (amino terminus). For the purposes of the design of a hybridization probe suitable for antiparallel binding to the target sequence (the preferred orientation), the N-terminus of the probing nucleobase sequence of the PNA probe is the equivalent of the 5'-hydroxyl terminus of an equivalent DNA or RNA oligonucleotide.

PNA Labeling/Modification:

Non-limiting methods for labeling PNAs are described in U.S. Pat. No. 6,110,676, U.S. Pat. No. 6,280,964, U.S. Pat. No. 6,355,421, U.S. Pat. No. 6,485,901, U.S. Pat. No. 6,361,942, and U.S. Pat. No. 6,441,152 (all of which are herein incorporated by reference), the examples section of this specification or are otherwise well known in the art of PNA synthesis and peptide synthesis. Methods for labeling PNA are also discussed in Nielsen et al., *Peptide Nucleic Acids; Protocols and Applications*, Horizon Scientific Press, Norfolk, England (1999). Non-limiting methods for labeling PNA oligomers are discussed below.

Because the synthetic chemistry of assembly is essentially the same, any method commonly used to label a peptide can often be adapted to effect the labeling a PNA oligomer. Generally, the N-terminus of the polymer can be labeled by reaction with a moiety having a carboxylic acid group or activated carboxylic acid group. One or more spacer moieties can optionally be introduced between the labeling moiety and the nucleobase containing subunits of the oligomer. Generally, the spacer moiety can be incorporated prior to performing the labeling reaction. If desired, the spacer may be embedded within the label and thereby be incorporated during the labeling reaction.

Typically the C-terminal end of the polymer can be labeled by first condensing a labeled moiety or functional group moiety with the support upon which the PNA oligomer is to be assembled. Next, the first nucleobase containing synthon of the PNA oligomer can be condensed with the labeled moiety or functional group moiety. Alternatively, one or more spacer moieties (e.g. 8-amino-3,6-dioxaoctanoic acid; the "O-linker") can be introduced between the label moiety or functional group moiety and the first nucleobase subunit of the oligomer. Once the molecule to be prepared is completely assembled, labeled and/or modified, it can be cleaved from the support deprotected and purified using standard methodologies.

For example, the labeled moiety or functional group moiety can be a lysine derivative wherein the ε-amino group is a protected or unprotected functional group or is otherwise modified with a reporter moiety. The reporter moiety could be a fluorophore such as 5(6)-carboxyfluorescein or a fluorescent or non-fluorescent quencher moiety such as 4-((4-(dimethylamino)phenyl)azo)benzoic acid (dabcyl). Condensation of the lysine derivative with the synthesis support can be accomplished using standard condensation (peptide) chemistry. The α-amino group of the lysine derivative can then be deprotected and the nucleobase sequence assembly initiated by condensation of the first PNA synthon with the α-amino group of the lysine amino acid. As discussed above, a spacer moiety may optionally be inserted between the lysine amino acid and the first PNA synthon by condensing a suitable spacer (e.g. Fmoc-8-amino-3,6-dioxaoctanoic acid) with the lysine amino acid prior to condensation of the first PNA synthon.

Alternatively, a functional group on the assembled, or partially assembled, polymer can be introduced while the oligomer is still support bound. The functional group can then be available for any purpose, including being used to either attached the oligomer to a support or otherwise be reacted with a reporter moiety, including being reacted post-ligation (by post-ligation we mean at a point after the oligomer has been fully formed by the performing of one or more condensation/ligation reactions). This method, however, requires that an appropriately protected functional group be incorporated into the oligomer during assembly so that after assembly is completed, a reactive functional can be generated. Accordingly, the protected functional group can be attached to any position within the oligomer, including, at the oligomer termini, at a position internal to the oligomer, or linked at a position internal to the linker.

For example, the ε-amino group of a lysine could be protected with a 4-methyl-triphenylmethyl (Mtt), a 4-methoxytriphenylmethyl (MMT) or a 4,4'-dimethoxytriphenylmethyl (DMT) protecting group. The Mtt, MMT or DMT groups can be removed from the oligomer (assembled using commercially available Fmoc PNA monomers and polystyrene support having a PAL linker; PerSeptive Biosystems, Inc., Framingham, Mass.) by treatment of the synthesis resin under mildly acidic conditions. Consequently, a donor moiety, acceptor moiety or other reporter moiety, for example, can then be condensed with the ε-amino group of the lysine amino acid while the polymer is still support bound. After complete assembly and labeling, the polymer can be then cleaved from the support, deprotected and purified using well-known methodologies.

By still another method, the reporter moiety can be attached to the oligomer after it is fully assembled and cleaved from the support. This method is useful where the label is incompatible with the cleavage, deprotection or purification regimes commonly used to manufacture the oligomer. By this method, the PNA oligomer will generally be labeled in solution by the reaction of a functional group on the polymer and a functional group on the label. Those of ordinary skill in the art will recognize that the composition of the coupling solution will depend on the nature of oligomer and label, such as, for example, a donor or acceptor moiety. The solution may comprise organic solvent, water or any combination thereof. Generally, the organic solvent will be a polar non-nucleophilic solvent. Non-limiting examples of suitable organic solvents include acetonitrile (ACN), tetrahydrofuran, dioxane, methyl sulfoxide, N,N'-dimethylformamide (DMF) and N-methylpyrrolidone (NMP).

The functional group on the polymer to be labeled can be a nucleophile (e.g. an amino group) and the functional group on the label can be an electrophile (e.g. a carboxylic acid or activated carboxylic acid). It is however contemplated that this can be inverted such that the functional group on the polymer can be an electrophile (e.g. a carboxylic acid or activated carboxylic acid) and the functional group on the label can be a nucleophile (e.g. an amino acid group). Non-limiting examples of activated carboxylic acid functional groups include N-hydroxysuccinimidyl esters. In aqueous solutions, the carboxylic acid group of either of the PNA or label (depending on the nature of the components chosen) can be activated with a water-soluble carbodiimide. The reagent, 1-ethyl-3-(3-dimethylamino-propyl)carbodiimide hydrochloride (EDC), is a commercially available reagent sold specifically for aqueous amide forming condensation reactions. Such condensation reactions can be improved when 1-Hydroxy-7-azabenzotriazole (HOAt) or 1-hydrozybenzotriazole (HOBt) is mixed with the EDC.

The pH of aqueous solutions can be modulated with a buffer during the condensation reaction. For example, the pH during the condensation can be in the range of 4-10. Generally, the basicity of non-aqueous reactions will be modulated by the addition of non-nucleophilic organic bases. Non-limiting examples of suitable bases include N-methylmorpholine, triethylamine and N,N-diisopropylethylamine. Alternatively, the pH can be modulated using biological buffers such as (N-[2-hydroxyethyl]piperazine-N'-[2-ethanesulfonic acid) (HEPES) or 4-morpholineethane-sulfonic acid (MES) or inorganic buffers such as sodium bicarbonate.

Labels:

Non-limiting examples of detectable moieties (labels) suitable for labeling PNA oligomers or antibodies used in the practice of this invention can include a dextran conjugate, a branched nucleic acid detection system, a chromophore, a fluorophore, a spin label, a radioisotope, an enzyme, a hapten, an acridinium ester and a chemiluminescent compound. Other suitable labeling reagents and methods of attachment would be recognized by those of ordinary skill in the art of PNA, peptide or nucleic acid synthesis.

Non-limiting examples of haptens include 5(6)-carboxyfluorescein, 2,4-dinitrophenyl, digoxigenin, and biotin.

Non-limiting examples of fluorochromes (fluorophores) include 5(6)-carboxyfluorescein (Flu), 6-((7-amino-4-methylcoumarin-3-acetyl)amino)hexanoic acid (Cou), 5(and 6)-carboxy-X-rhodamine (Rox), Cyanine 2 (Cy2) Dye, Cyanine 3 (Cy3) Dye, Cyanine 3.5 (Cy3.5) Dye, Cyanine 5 (Cy5) Dye, Cyanine 5.5 (Cy5.5) Dye Cyanine 7 (Cy7) Dye, Cyanine 9 (Cy9) Dye (Cyanine dyes 2, 3, 3.5, 5 and 5.5 are available as NHS esters from Amersham, Arlington Heights, Ill.) or the Alexa dye series (Molecular Probes, Eugene, Oreg.).

Non-limiting examples of enzymes include polymerases (e.g. Taq polymerase, Klenow PNA polymerase, T7 DNA polymerase, Sequenase, DNA polymerase 1 and phi29 polymerase), alkaline phosphatase (AP), horseradish peroxidase (HRP), soy bean peroxidase (SBP)), ribonuclease and protease.

Energy Transfer

In one embodiment, PNA oligomers can be labeled with an energy transfer set. For energy transfer to be useful in determining hybridization, there should be an energy transfer set comprising at least one energy transfer donor and at least one energy transfer acceptor moiety. Often, the energy transfer set will include a single donor moiety and a single acceptor moiety, but this is not a limitation. An energy transfer set may contain more than one donor moiety and/or more than one acceptor moiety. The donor and acceptor moieties operate such that one or more acceptor moieties accepts energy transferred from the one or more donor moieties or otherwise quenches the signal from the donor moiety or moieties. Thus, in one embodiment, both the donor moiety(ies) and acceptor moiety(ies) are fluorophores. Though the previously listed fluorophores (with suitable spectral properties, where appropriate) might also operate as energy transfer acceptors, the acceptor moiety can also be a non-fluorescent quencher moiety such as 4-((-4-(dimethylamino)phenyl)azo) benzoic acid (dabcyl). The labels of the energy transfer set can be linked at the oligomer termini or linked at a site within the oligomer. In one embodiment, each of two labels of an energy transfer set can be linked at the distal-most termini of the oligomer.

Transfer of energy between donor and acceptor moieties may occur through any energy transfer process, such as through the collision of the closely associated moieties of an energy transfer set(s) or through a non-radiative process such as fluorescence resonance energy transfer (FRET). Transfer of energy between the donor and acceptor moieties may occur through an as yet defined mechanism.

For FRET to occur, transfer of energy between donor and acceptor moieties of a energy transfer set requires that the moieties be close in space and that the emission spectrum of a donor(s) have substantial overlap with the absorption spectrum of the acceptor(s) (See: Yaron et al. *Analytical Biochemistry*, 95: 228-235 (1979) and particularly page 232, col. 1 through page 234, col. 1). Alternatively, collision mediated (radiationless) energy transfer may occur between very closely associated donor and acceptor moieties whether or not the emission spectrum of a donor moiety(ies) has a substantial overlap with the absorption spectrum of the acceptor moiety(ies) (See: Yaron et al., *Analytical Biochemistry*, 95: 228-235 (1979) and particularly page 229, col. 1 through page 232, col. 1). This process is referred to as intramolecular collision since it is believed that quenching is caused by the direct contact of the donor and acceptor moieties (See: Yaron et al.). It is to be understood that any reference to energy transfer in the instant application encompasses all of these mechanistically distinct phenomena. It is also to be understood that energy transfer can occur though more than one energy transfer process simultaneously and that the change in detectable signal can be a measure of the activity of two or more energy transfer processes. Accordingly, the mechanism of energy transfer is not a limitation of this invention.

Detecting Energy Transfer In A Self-Indicating PNA Oligomer:

When labeled with an energy transfer set, we refer to the PNA oligomer as being self-indicating. In one embodiment, a self-indicating oligomer can be labeled in a manner that is described in U.S. Pat. No. 6,475,721 entitled: "Methods, Kits And Compositions Pertaining To Linear Beacons" and the related PCT application which has also now published as WO99/21881, both of which are hereby incorporated by reference.

Hybrid formation between a self-indicating oligomer and a target sequence can be monitored by measuring at least one physical property of at least one member of the energy transfer set that is detectably different when the hybridization complex is formed as compared with when the oligomer exists in a non-hybridized state. We refer to this phenomenon as the self-indicating property of the oligomer. This change in detectable signal results from the change in efficiency of energy transfer between donor and acceptor moieties caused by hybridization of the oligomer to the target sequence.

For example, the means of detection can involve measuring fluorescence of a donor or acceptor fluorophore of an energy transfer set. In one embodiment, the energy transfer set may comprise at least one donor fluorophore and at least one acceptor (fluorescent or non-fluorescent) quencher such that the measure of fluorescence of the donor fluorophore can be used to detect, identify or quantitate hybridization of the oligomer to the target sequence. For example, there may be a measurable increase in fluorescence of the donor fluorophore upon the hybridization of the oligomer to a target sequence.

In another embodiment, the energy transfer set comprises at least one donor fluorophore and at least one acceptor fluorophore such that the measure of fluorescence of either, or both, of at least one donor moiety or one acceptor moiety can be used to can be used to detect, identify and/or quantitate hybridization of the oligomer to the target sequence.

Self-indicating PNA oligomers can be used in in-situ hybridization assays. However, self-indicating PNA oligomers are particularly well suited for the analysis nucleic acid amplification reactions (e.g. PCR) either in real-time or at the end point (See For Example: U.S. Pat. No. 6,485,901).

Determining Energy Transfer In A Detection Complex:

In another embodiment, the PNA oligomers of the present invention can be labeled solely with a quencher moiety and can be used as a component oligomer in a Detection Complex as more fully explained in U.S. Pat. No. 6,361,942 entitled: "Methods, Kits And Compositions Pertaining To Detection Complexes" and the related PCT application that has also now published as WO99/49293, both of which are herein incorporated by reference. When the Detection Complex is formed, at least one donor moiety of one component polymer is brought sufficiently close in space to at least one acceptor moiety of a second component polymer. Since the donor and acceptor moieties of the set are closely situated in space, transfer of energy occurs between moieties of the energy transfer set. When the Detection Complex dissociates, as for example when one of the component polymers of the Detection Complex hybridize to a target sequence, the donor and acceptor moieties do not interact sufficiently to cause substantial transfer of energy from the donor and acceptor moieties of the energy transfer set and there is a correlating change in detectable signal from the donor and/or acceptor moieties of the energy transfer set. Consequently, Detection Complex formation/dissociation can be determined by measuring at least one physical property of at least one member of the energy transfer set that is detectably different when the complex is formed as compared with when the component polymers of the Detection Complex exist independently and unassociated.

Detectable And Independently Detectable Moieties/Multiplex Analysis:

In certain embodiments of this invention, a multiplex hybridization assay is performed. In a multiplex assay, numerous conditions of interest are simultaneously or sequentially examined. Multiplex analysis relies on the ability to sort sample components or the data associated therewith, during or after the assay is completed. In performing a multiplex assay, one or more distinct independently detectable moieties can be used to label two or more different oligomers that are to be used in an assay. By independently detectable we mean that it is possible to determine one label independently of, and in the presence of, the other label. The ability to differentiate between and/or quantitate each of the independently detectable moieties provides the means to multiplex a hybridization assay because the data correlates with the hybridization of each of the distinct, independently labeled oligomer to a particular target sequence sought to be detected in the sample. Consequently, the multiplex assays of this invention can, for example, be used to simultaneously or sequentially detect the presence, absence, number, position and/or identity of two or more target sequences in the same sample and in the same assay. For example, the PNA oligomers of a oligomer set can be used in a multiplex assay when the oligomers are independently detectable (e.g. labeled with independently detectable fluorophores) and comprise different probing nucleobase sequences wherein each probe can be used to interrogate the same sample, simultaneously or sequentially, for a different target sequence of interest.

Spacer/Linker Moieties:

Generally, spacers are used to minimize the adverse effects that bulky labeling reagents might have on hybridization properties of probes. Linkers may introduce flexibility and randomness into the probe or otherwise link two or more nucleobase sequences of a probe or component polymer. Preferred spacer/linker moieties for the nucleobase polymers of this invention consist of one or more aminoalkyl carboxylic acids (e.g. aminocaproic acid) the side chain of an amino acid (e.g. the side chain of lysine or ornithine) natural amino acids (e.g. glycine), aminooxyalkylacids (e.g. 8-amino-3,6-dioxaoctanoic acid), alkyl diacids (e.g. succinic acid), alkyloxy diacids (e.g. diglycolic acid) or alkyldiamines (e.g. 1,8-diamino-3,6-dioxaoctane). Spacer/linker moieties may also incidentally or intentionally be constructed to improve the water solubility of the probe (For example see: Gildea et al., Tett. Lett. 39: 7255-7258 (1998)). Preferably, a spacer/linker moiety comprises one or more linked compounds having the formula: $-Y-(O_m-(CW_2)_n)_o-Z-$. The group Y is selected from the group consisting of: a single bond, $-(CW_2)_p-$, $-C(O)(CW_2)_p-$, $-C(S)(CW_2)_p-$ and $-S(O_2)(CW_2)_p$. The group Z has the formula NH, $NR^2$, S or O. Each W is independently H, $R^2$, $-OR^2$, F, Cl, Br or I; wherein, each $R^2$ is independently selected from the group consisting of: $-CX_3$, $-CX_2CX_3$, $-CX_2CX_2CX_3$, $-CX_2CX(CX_3)_2$, and $-C(CX_3)_3$. Each X is independently H, F, Cl, Br or I. Each m is independently 0 or 1. Each n, o and p are independently integers from 0 to 10.

Hybridization Conditions/Stringency:

Those of ordinary skill in the art of hybridization will recognize that factors commonly used to impose or control stringency of hybridization include formamide concentration (or other chemical denaturant reagent), salt concentration (i.e., ionic strength), hybridization temperature, detergent concentration, pH and the presence or absence of chaotropes. Optimal stringency for a oligomer/target sequence combination is often found by the well-known technique of fixing several of the aforementioned stringency factors and then determining the effect of varying a single stringency factor. The same stringency factors can be modulated to thereby control the stringency of hybridization of a PNA to a nucleic acid, except that the hybridization of a PNA is fairly independent of ionic strength. Optimal or suitable stringency for an assay may be experimentally determined by examination of each stringency factor until the desired degree of discrimination is achieved.

Suitable Hybridization Conditions:

Generally, the more closely related the background causing nucleic acid contaminates are to the target sequence, the more carefully stringency must be controlled. Blocking probes may also be used as a means to improve discrimination beyond the limits possible by mere optimization of stringency factors. Suitable hybridization conditions will thus comprise conditions under which the desired degree of discrimination is achieved such that an assay generates an accurate (within the tolerance desired for the assay) and reproducible result. Often this is achieved by adjusting stringency until sequence specific hybridization of the probe and target sequence is achieved. In the present invention, it may be preferable to perform the assay under denaturing conditions. For example, the assay can be performed under low salt (e.g. less than 100 mM total ionic strength), in the presence of formamide, immediately after heat denatuation, or any combination of the foregoing. Nevertheless, aided by no more than routine experimentation and the disclosure provided herein, those of skill in the art will be able to determine suitable hybridization conditions for performing assays utilizing the methods and compositions described herein.

Blocking Probes:

Blocking probes are nucleic acid or non-nucleic acid oligomers (e.g. PNA oligomers) that can be used to suppress the binding of the probing nucleobase sequence of the oligomer to a non-target sequence. Preferred blocking probes are PNA probes (See: Coull et al., U.S. Pat. No. 6,110,676, herein incorporated by reference).

Typically, blocking probes are closely related to the probing nucleobase sequence and preferably they comprise one or more single point mutations as compared with the target sequence sought to be detected in the assay. It is believed that blocking probes operate by hybridization to the non-target sequence to thereby form a more thermodynamically stable complex than is formed by hybridization between the probing nucleobase sequence and the non-target sequence. Formation of the more stable and preferred complex blocks formation of the less stable non-preferred complex between the probing nucleobase sequence and the non-target sequence. Thus, blocking probes can be used with the methods and compositions of this invention to suppress the binding of the nucleic acid or non-nucleic acid oligomer (e.g. PNA probes) to a non-target sequence that might be present in an assay and thereby interfere with the performance of the assay. (See: Fiandaca et al. "*PNA Blocker Probes Enhance Specificity In Probe Assays*", Peptide Nucleic Acids: Protocols and Applications, pp. 129-141, Horizon Scientific Press, Wymondham, UK, 1999). For example, a PNA oligomer of Seq. ID No. 3 (TTC-AAT-GGC-TCC-CGC) can be combined (e.g. in a kit or set) as a blocker probe with a PNA oligomer of Seq. ID No. 2 (TTC-AAA-GGC-TCC-CGC) to thereby increase the accuracy of an assay (See: Example 1).

Probing Nucleobase Sequence:

The probing nucleobase sequence of a PNA oligomer is the specific sequence recognition portion of the construct. Therefore, the probing nucleobase sequence is a sequence of PNA subunits designed to sequence specifically hybridize to a target sequence wherein the presence, absence and/or amount of target sequence/PNA oligomer complex that forms can be used to determine the presence, absence and/or number of organisms or spores of *Bacillus anthracis* of interest in a sample. Consequently, with due consideration of the requirements of a PNA oligomer for the assay format chosen, the length of the probing nucleobase sequence of the PNA probe will generally be chosen such that a stable complex is formed with the target sequence under suitable hybridization conditions.

The probing nucleobase sequence suitable for determining *Bacillus anthracis* can have a length of 18 or fewer PNA subunits. The probing nucleobase sequence can comprise a nucleobase sequence that is at least 90% homologous to either of: CCA-SSG-GTA-TCD-DTC (Seq. ID No. 1) or TTC-AAA-GGC-TCC-CGC (Seq. ID No. 2). The PNA oligomers can comprise the exact nucleobase sequence that is one hundred percent homologous to Seq. ID No. 1 or Seq. ID No. 2 or even be exactly Seq. ID No. 1 or Seq. ID No. 2. Complements of the probing nucleobase sequences identified above are included since it is possible to prepare or amplify copies of the target sequence wherein the copies are complements of the target sequence and thus, will bind to the complement of Seq. ID. No. 1 or Seq. ID No. 2.

A PNA probe of this invention will generally have a probing nucleobase sequence that is complementary to the target sequence. Alternatively, a substantially complementary probing nucleobase sequence might be used since it has been demonstrated that greater sequence discrimination can be obtained when utilizing probes wherein there exists one or more point mutations (base mismatch) between the probe and the target sequence (See: Guo et al., *Nature Biotechnology* 15:331-335 (1997)).

This invention contemplates that variations in Seq. ID. No. 1 or Seq. ID No. 2 can provide PNA oligomers that are suitable for the specific detection of *Bacillus anthracis*. Common variations include, deletions, insertions and frame shifts. Variation of the probing nucleobase sequences within the parameters described herein are considered to be an embodiment of this invention.

Oligomer Probe Complexes:

In still another embodiment, two probes are designed to hybridize to the target sequence sought to be detected to thereby generate a detectable signal whereby the probing nucleobase sequence of each probe comprises half or approximately half of the complete target sequence of the organism sought to be detected in the assay. Accordingly, in one embodiment, the probing nucleobase sequence is distributed between two different oligomers, or between two oligomer blocks of a combination oligomer. As a non-limiting example, the probing nucleobase sequences of the two oligomers might be designed using the assay as described in U.S. Pat. No. 6,027,893, herein incorporated by reference. Using this methodology, the probes that hybridize to the target sequence may or may not be labeled. However, it is the probe complex formed by the annealing of the adjacent probes that is detected. Similar compositions comprised solely of PNA have been described in copending U.S. Pat. No. 6,287,772, herein incorporated by reference. As another non-limiting example, the probing nucleobase sequence can be distributed between oligomer blocks of a combination oligomer as described in co-pending application U.S. Ser. No. 10/096,125, filed Mar. 9, 2002, herein incorporated by reference.

Immobilization Of PNA Oligomers To A Solid Support Or Surface:

One or more of the oligomers of this invention may optionally be immobilized to a surface or solid support for the detection of a target sequence. Immobilization can, for example, be used in capture assays or to prepare arrays.

The oligomers can be immobilized to a surface using the well-known process of UV-crosslinking. The oligomers can also be synthesized on the surface in a manner suitable for deprotection but not cleavage from the synthesis support (See: Weiler, J. et al, Hybridization based DNA screening on peptide nucleic acid (PNA) oligomer arrays, Nucl. Acids Res., 25, 14:2792-2799 (July 1997)). In still another embodiment, one or more oligomers can be covalently linked to a surface by the reaction of a suitable functional group on the oligomer with a functional group of the surface (See: Lester, A. et al, "PNA Array Technology": Presented at Biochip Technologies Conference in Annapolis (October 1997)). This method is advantageous as compared to several of the other methods since the oligomers deposited on the surface for immobilization can be highly purified and attached using a defined chemistry, thereby possibly minimizing or eliminating non-specific interactions.

Methods for the chemical attachment of PNA oligomers to surfaces may involve the reaction of a nucleophilic group, (e.g. an amine or thiol) of the probe to be immobilized, with an electrophilic group on the support to be modified. Alternatively, the nucleophile can be present on the support and the electrophile (e.g. activated carboxylic acid) present on the oligomer. Because native PNA possesses an amino terminus, a PNA may or may not require modification to thereby immobilize it to a surface (See: Lester et al., Poster entitled "PNA Array Technology").

Conditions suitable for the immobilization of an oligomer to a surface will generally be similar to those conditions suitable for the labeling of the polymer. The immobilization reaction is essentially the equivalent of labeling whereby the label is substituted with the surface to which the polymer is to be linked (see above).

Numerous types of solid supports derivatized with amino groups, carboxylic acid groups, isocyantes, isothiocyanates and malimide groups are commercially available. Non-limiting examples of suitable solid supports include membranes, glass, controlled pore glass, polystyrene particles (beads), silica and gold nanoparticles. All of the above recited methods of immobilization are not intended to be limiting in any way but are merely provided by way of illustration.

Arrays Of PNA Oligomers Or Oligomer Sets:

Arrays are surfaces to which two or more oligomers have been immobilized each at a specified position. The probing nucleobase sequence of the immobilized oligomers can be judiciously chosen to interrogate a sample that may contain one or more target organisms. Because the location and composition of each immobilized probe can be known, arrays can be useful for the simultaneous detection, identification and/or quantitation of the nucleic acid of two or more organisms that may be present in the sample. Moreover, arrays of PNA probes can be regenerated by stripping the hybridized nucleic acid after each assay, thereby providing a means to repetitively analyze numerous samples using the same array (See for example: U.S. Pat. No. 6,475,721), herein incorporated by reference). Thus, arrays of PNA oligomers or PNA oligomer sets may be useful for preparing arrays, including use for the repetitive screening of samples for target organisms of interest.

II. Embodiments of the Invention

This invention is directed to PNA oligomers, oligomer sets, methods and/or kits useful for detecting, identifying and/or quantitating (enumerating) *Bacillus anthracis*, or the rRNA or rDNA associated therewith.

a. PNA Oligomers:

In one embodiment, this invention pertains to PNA oligomers. The PNA oligomers of this invention can be used to detect, identify and/or quantitate *Bacillus anthracis*, or the rRNA or rDNA associated therewith. A PNA oligomer of this invention can comprise a probing nucleobase sequence, wherein at least a portion of the probing nucleobase sequence is at least ninety percent homologous to the nucleobase sequences, or their complements, selected from the group consisting of: CCA-SSG-GTA-TCD-DTC (Seq. ID No. 1) and TTC-AAA-GGC-TCC-CGC (Seq. ID No. 2). These sequences target the only two known point mutation differences of the 23S rRNA of *Bacillus anthracis* as compared with other organisms (See: Ash et al., *FEMS Microbiology Letters,* 94: 75-80 (1992).

A PNA oligomer of this invention can be a PNA oligomer that comprises one or more non-natural nucleobases so that the PNA oligomer does not substantially intra or inter molecularly self-hybridize. The PNA oligomer can be designed to be capable of sequence-specifically hybridizing to a target sequence within the nucleic acid of *Bacillus anthracis*, or the rRNA or rDNA associated therewith. It is to be understood that the foregoing characteristics are not mutually exclusive.

The PNA oligomers of this invention may comprise only a probing nucleobase sequence (as previously described herein) or may comprise additional moieties. Non-limiting examples of additional moieties include detectable moieties (labels), linkers, spacers, natural or non-natural amino acids, peptides, enzymes and/or other subunits of PNA, DNA or RNA. Additional moieties may be functional or non-functional in an assay. Generally however, additional moieties will be selected to be functional within the design of an assay for the determination of *Bacillus anthracis.*

For example, a PNA oligomer can be labeled with one or more detectable moieties. One or more of the oligomers can be labeled with two or more independently detectable moieties, particularly when used in sets comprising numerous probes wherein it is important that each PNA oligomer comprises a unique label when used in a multiplex assay. The independently detectable moieties can be independently detectable fluorophores.

The oligomers of this invention can be used in in-situ hybridization (ISH) and fluorescence in-situ hybridization (FISH) assays. Excess probe used in a ISH or FISH assay can be removed by washing after the sample has been incubated with probe for a period of time so that the detectable moiety of specifically bound oligomer probe can be detected above the background signal that results from any still present but unhybridized oligomer probe. However, self-indicating probes can be used to minimize or avoid this requirement since excess self-indicating oligomer can be designed to be essentially non-fluorescent until it hybridizes to a target sequence such that minimal detectable background signal is generated from unhybridized oligomer.

Unlabeled Non-Nucleic Acid Probes:

The PNA oligomers of this invention need not be labeled with a detectable moiety to be operable within the methods of this invention. Accordingly, the PNA oligomers of this invention can be unlabeled.

When using the PNA oligomers of this invention it is possible to detect the probe/target sequence complex formed by hybridization of the probing nucleobase sequence of the oligomer to the target sequence. For example, a PNA/nucleic acid complex formed by the hybridization of a probing nucleobase sequence to the target sequence can be detected using an antibody or antibody fragment that specifically interacts with the complex under antibody binding conditions. Suitable antibodies to PNA/nucleic acid complexes and methods for preparation and use are described in U.S. Pat. No. 5,612,458, herein incorporated by reference.

The antibody/PNA/nucleic acid complex formed by interaction of the α-PNA/nucleic acid antibody with the PNA/nucleic acid complex can be detected by several methods. For example, the α-PNA/nucleic acid antibody can be labeled with a detectable moiety. Suitable detectable moieties have been previously described herein. Thus, the presence, absence and/or quantity of the detectable moiety can be correlated with the presence, absence and/or quantity of the antibody/PNA/nucleic acid complex and the *Bacillus anthracis*, or the rRNA or rDNA associated therewith, sought to be determined.

Alternatively, the antibody/PNA/nucleic acid complex can be detected using one or more secondary antibodies at least one of which is labeled with a detectable moiety. Typically the secondary antibody or antibodies specifically bind to the α-PNA/nucleic acid antibody under antibody binding conditions. Thus, the presence, absence and/or quantity of the detectable moiety of at least one of the secondary antibodies can be correlated with the presence, absence and/or quantity of the antibody/antibody/PNA/nucleic acid complex and the *Bacillus anthracis*, or the rRNA or rDNA associated therewith, sought to be determined. As used herein, the term antibody shall include antibody fragments that specifically bind to other antibodies or other antibody fragments.

b. PNA Probe Sets:

In another embodiment, this invention pertains to oligomer sets. For example, an oligomer set can comprise two or more oligomers, at least one of which is a PNA oligomer that comprises a probing nucleobase sequence that is at least ninety percent homologous to the nucleobase sequences, or their complements, selected from the group consisting of: CCA-SSG-GTA-TCD-DTC (Seq. ID No. 1) and TTC-AAA-GGC-TCC-CGC (Seq. ID No. 2). The PNA oligomer set can be a set comprising two or more PNA oligomers, at least one of which is a PNA oligomer that comprises one or more non-natural nucleobases so that the PNA oligomer does not substantially intra or inter molecularly self-hybridize. The PNA oligomer can be designed to be capable of sequence-specifically hybridizing to a target sequence within the nucleic acid of *Bacillus anthracis* of the rRNA or rDNA associated therewith.

The grouping of PNA oligomers within sets characterized for specific groups of organisms can be a very useful embodiment of this invention. Thus, the PNA oligomers of this invention can be combined with probes for other organisms such as yeast. For example, the analysis of yeast using PNA probes has been described in U.S. Pat. No. 6,280,946, herein incorporated by reference, wherein a multiplex assay for both yeast and bacteria has been described using a PNA probe set. Accordingly, an exemplary probe set might include probes for the determination of *Bacillus anthracis* as well as other probes for bacteria or yeast.

Probe sets of this invention comprise at least one PNA oligomer but need not comprise only PNA oligomers. For example, oligomer sets of this invention can comprise mixtures of PNA oligomers and nucleic acid oligomers, provided however that a set comprises at least one PNA oligomer described herein.

The oligomers of a set need not all be directed solely to a target sequence of an organism to be determined. For example, one or more of the oligomers of a set can be blocking probes. In this regard some of the oligomers of a set can be labeled whilst others are unlabeled such as when unlabeled blocking probes are used in combination with labeled oligomers for the in-situ determination of a target organism such as *Bacillus anthracis*.

The oligomers of a set need not all be of the same length. It is to be understood that the oligomers of a set will typically be selected to perform an assay. Accordingly, the characteristics of the oligomers of set can be selected to thereby optimize an assay. Thus, the physical characteristics of the oligomers can be accordingly selected.

c. Methods:

In yet another embodiment, this invention pertains to methods for determining *Bacillus anthracis*, or the rRNA or rDNA associated therewith. Determining the nucleic acid characteristic for *Bacillus anthracis* can be used to detect, identify and/or quantitate (enumerate) *Bacillus anthracis* spores and/or organisms. The characteristics of PNA probes suitable for the detection, identification and/or quantitation of *Bacillus anthracis* have been previously described herein.

In one embodiment, the method can comprise contacting the sample, under suitable hybridization conditions, with at least one PNA oligomer that comprises one or more non-natural nucleobases so that the PNA oligomer does not substantially intra or inter molecularly self-hybridize. The PNA oligomer can be designed to be capable of sequence-specifically hybridizing to a target sequence within the nucleic acid of *Bacillus anthracis*. According to the method, hybridization of the probing nucleobase sequence to the target sequence is detected, identified and/or quantitated. Because hybridization requires sequence specific complex formation between the target sequence and the PNA oligomer, the result can be correlated with the presence, absence and/or quantity of *Bacillus anthracis* in the sample. This correlation is possible because the determination of specific complex formation between the target sequence and the PNA oligomer can be correlated with the presence, absence and/or quantity of *Bacillus anthracis*, or the rRNA or rDNA associated therewith, in the sample.

PNA oligomers comprising non-natural nucleobases that are capable of destabilizing inter and intra molecular interactions have been described (See: The Principles of Non-Complementarity, Ph.D. Thesis of Jesper Lohse, Faculty of Science, University of Copenhagen; Also see Lohse et al., PNAS, 96 (21): 11804-11808 (1999)). Accordingly, the non-natural nucleobases can be selected from 2-thiothymine, 2-thiouridine (one letter code S as used herein) or N9-(2,6-diaminopurine) (one letter code D as used herein). It has been demonstrated that although oligomers comprising these nucleobases do not substantially intra or intermolecularly interact, they are capable of hybridizing to complementary nucleic acid wherein 2-thiothymine or 2-thiouridine base pair with adenine and N9-(2,6-diaminopurine) base pairs with thymine or uracil.

PNA oligomers comprising 2-thiothymine or 2-thiouridine and/or N9-(2,6-diaminopurine) can be very advantageously used under denaturing conditions. Under denaturing conditions, such as under conditions of low ionic strength, the nucleic acid to be targeted will not substantially self-anneal even when it is highly self-complementary. Since it is denatured, the PNA oligomer can very easily hybridize to the target sequence, if present. (See: Stefano et al., Diagnostic Gene Detection and Quantification Technologies for Infectious Agents and Human Genetic Diseases, #948 IBC Library Series, 19-37 (1997).

In yet another embodiment, a method for determining the rRNA of *Bacillus anthracis* can comprise contacting the sample, under suitable hybridization conditions, with at least one PNA oligomer comprising a probing nucleobase sequence that is at least ninety percent homologous to the nucleobase sequences, or their complements, selected from the group consisting of: CCA-SSG-GTA-TCD-DTC (Seq. ID No. 1) and TTC-AAA-GGC-TCC-CGC (Seq. ID No. 2). Sequence specific hybridization of the probing nucleobase sequence of a PNA oligomer to a target sequence within the rRNA of *Bacillus anthracis* can be detected, identified and/or quantitated. Because hybridization requires sequence specific complex formation between the target sequence and the PNA oligomer, the result can be correlated with the presence, absence and/or quantity of *Bacillus anthracis* in the sample.

d. Kits:

In still another embodiment, this invention pertains to kits for determining the presence, absence and/or number of *Bacillus anthracis* in a sample. The kit can comprise one or more PNA oligomers. The PNA oligomers can comprise a probing nucleobase sequence that is at least ninety percent homologous to the nucleobase sequences, or their complements, selected from the group consisting of: CCA-SSG-GTA-TCD-DTC (Seq. ID No. 1), TTC-AAA-GGC-TCC-CGC (Seq. ID No. 2) and TTC-AAT-GGC-TCC-CGC (Seq. ID No. 3). The kit can comprise other reagents, instructions or compositions necessary to perform an assay. The kit can comprise a PNA oligomer that comprises one or more non-natural nucleobases so that the PNA oligomers do not substantially intra or inter molecularly self-hybridize. The PNA oligomers can be designed to sequence-specifically hybridize to a target sequence within the nucleic acid of *Bacillus anthracis*, including the rRNA or rDNA associated therewith. The other characteristics of PNA oligomers suitable for the detection, identification and/or quantitation of *Bacillus anthracis* have been previously described herein.

The kits can, for example, be used for in-situ assays or for use with nucleic acid amplification technologies. Non-limiting examples of nucleic acid amplification technologies include, but are not limited to, Polymerase Chain Reaction (PCR), Ligase Chain Reaction (LCR), Strand Displacement Amplification (SDA), Transcription-Mediated Amplification (TMA), Q-beta replicase amplification (Q-beta) and Rolling Circle Amplification (RCA). Accordingly, in one embodiment the other reagents can comprise, buffers, enzymes and/or master mixes for performing an in-situ or nucleic acid amplification based assay.

The kits of this invention comprise one or more PNA oligomers and other reagents or compositions that are selected to perform an assay or otherwise simplify the performance of an assay. In kits that contain sets of probes, wherein each of at least two probes of the set are used to detect at least one target organism other than *Bacillus anthracis*, the probes of the set can be labeled with one or more independently detectable moieties (e.g. independently detectable fluorophores) so that each specific target organism can be individually detected, identified and/or quantitated in a single assay.

e. Exemplary Assay Formats:

The probes, probe sets, methods and/or kits of this invention can be used for the detection, identification and/or quantitation of *Bacillus anthracis*. For example, in-situ hybridization can be used as the assay format for detecting, identifying and/or quantitating *Bacillus anthracis*. Fluorescence in-situ hybridization (FISH or PNA-FISH) can be the assay format. Specific PNA-FISH methods used to experimentally test specific PNA probes can be found in Example 1 of this specification and thereby demonstrates that labeled PNA oligomers can be used to very specifically determine *Bacillus anthracis* in a sample. The experimental conditions used in the Example yield results within approximately 3-4 hours.

For in-situ assays, *Bacillus anthracis* organisms can be fixed on slides and visualized with a film, camera, microscope or slide scanner. Alternatively, the organisms can be fixed in solution and then analyzed in a flow cytometer. Slide scanners and flow cytometers are particularly useful for rapidly quantitating the number of target organisms present in a sample of interest.

The probes, probe sets, methods and/or kits of this invention can be used with most any probe based method for the analysis of *Bacillus anthracis*. For example, the probes of this invention can be use in a no-wash method as described in more detail in copending application U.S. Ser. No. 10/017,445 filed on Dec. 14, 2001 and now published as WO02/57493.

f. Exemplary Applications For Using The Invention:

Since *Bacillus anthracis* can be a biowarfare pathogen, the PNA oligomers, oligomer sets, methods and/or kits of this invention can be useful for the determination of *Bacillus anthracis* in air, food, beverages, water, pharmaceutical products, personal care products, dairy products environmental samples, mail and/or packaging as well as in equipment used to process, store and/or handle any of the foregoing. Additionally, the PNA oligomers, oligomer sets, methods and/or kits of this invention can be useful for the determination of *Bacillus anthracis* in clinical samples and/or clinical environments. By way of a non-limiting example, the PNA oligomers, oligomer sets, methods and/or kits of this invention can be useful in the analysis of culture samples. Other non-limiting examples of clinical samples include: sputum, laryngeal swabs, gastric lavage, bronchial washings, biopsies, aspirates, expectorates, body fluids (e.g. spinal, pleural, pericardial, synovial, blood, pus, amniotic, and urine), bone marrow and tissue sections and cultures thereof. The PNA oligomers, oligomer sets, methods and/or kits can also be useful for the analysis of clinical specimens, equipment, fixtures or products used to treat humans or animals.

Having described the preferred embodiments of the invention, it will now become apparent to one of skill in the art that other embodiments incorporating the concepts described herein may be used. It is felt, therefore, that these embodiments should not be limited to disclosed embodiments but rather should be limited only by the spirit and scope of the invention.

EXAMPLES

This invention is now illustrated by the following examples that are not intended to be limiting in any way.

Example 1

Fluorescence in situ Hybridization Using PNA Probes Specific to the 23S rRNA of *Bacillus anthracis*

| PNA Probe | sequence |
|---|---|
| Bant23S02/Flu | Flu-OO-CCA-SSG-GTA-TCD-DTC-$NH_2$ |
| Bant23S03/Flu | Flu-OO-TTC-AAA-GGC-TCC-CGC-$NH_2$ |
| Bant23S03/BLK | H-TTC-AAT-GGC-TCC-CGC-$NH_2$ |

(Note: S = 2-thiouracil, D = N9-(2,6-diaminopurine); conventional peptide nomenclature used to illustrate the termini of the PNA oligomers; O = 8-amino-3,6-dioxaoctanoic acid)

Reference strains. Reference strains were obtained from American Type Culture Collection (ATCC), Manassas, Va. and the Deutsche Sammlung von Mikroorganismen und Zellkulturen GmbH, Braunschweig, Germany. Cultures of each strain were prepared using Tryptic soy broth or commercial blood culture bottles (BioMerieux, Hazelwood, Mo.).

Preparation of smears. One drop of phosphate-buffered saline (PBS) was placed in the well of a Teflon-coated microscope slide (Clear Coat, Erie Scientific, Portsmouth, N.H.) and 20 µL of culture was added, mixed and spread throughout the well. The smear was fixed by heat fixation or methanol fixation. The slide was subsequently immersed into 95% ethanol for 5-10 minutes and allowed to air-dry.

Fluorescence in situ hybridization using PNA probes (PNA FISH). Smears were covered with approximately 20 µL of hybridization solution containing 10% (w/v) dextran sulfate (Sigma Chemical Co., St. Louis, Mo.), 30% (v/v) formamide (Sigma), 0.1% (w/v) sodium pyrophosphate (Sigma), 0.2% (w/v) polyvinylpyrrolidone (Sigma), 0.2% (w/v) ficoll (Sigma), 5 mM Na$_2$EDTA (Sigma), 1% (v/v) Triton X-100 (Aldrich), 50 mM Tris/HCl pH 7.5 and either 250 nM Bant23S02/Flu or a mixture of 250 nM Bant23S03/Flu with 1000 nM Bant23S03/BLK. Coverslips were placed on the smears to ensure even coverage with hybridization solution, and the slides were placed on a slide warmer with a humidity chamber (Slidemoat, Boeckel, Germany) and incubated for 90 min at 55° C. Following hybridization, the coverslips were removed by submerging the slides into approximately 20 ml/slide of pre-warmed 5 mM Tris, pH 10, 15 mM NaCl (J. T. Baker), 0.1% (v/v) Triton X-100 (Aldrich) in a water bath at 55° C. and washed for 30 min. The slides were then air-dried. Each smear was finally mounted using one drop of IMAGEN Mounting Fluid (DAKO, Ely, UK) and covered with a coverslip. Microscopic examination was conducted using a fluorescence microscope using a FITC/Texas Red dual band filter set (Chroma Technology Corp., Brattleboro, Vt.).

TABLE 1

Results using a panel of reference strains and isolates representing clinically relevant and phylogenetically related bacterium and yeast species.

| Species | Strain ID | Bant23S03/Flu Bant23S03BLK | Bant23S02/ Flu |
|---|---|---|---|
| Bacillus anthracis | Sterne A15 | + | + |
| Bacillus brevis[a] | ATCC 8246 | − | − |
| Bacillus cereus | ATCC 13061 | + | − |
| Bacillus cereus[a] | DSM 31 | − | − |
| Bacillus lichenformis | ATCC 12759 | − | − |
| Bacillus lichenformis[a] | ATCC 14580 | − | − |
| Bacillus mycoides[a] | DSM 299 | − | − |
| Bacillus polymyxa[a] | ATCC 842 | + | − |
| Bacillus pseudomycoides[a] | DSM 12442 | + | − |
| Bacillus pseudomycoides | DSM 12443 | + | − |
| Bacillus sphaericus | ATCC 4525 | − | − |
| Bacillus stearothermophilus | ATCC 7953 | − | − |
| Bacillus subtilis | ATCC 6633 | − | − |
| Bacillus thuringiensis[a] | DSM 2046 | − | − |
| Bacillus weihenstephanensis[a] | DSM 11821 | − | − |
| Escherichia coli | ATCC 25922 | − | − |
| Pseudomonas aeruginosa | ATCC 27853 | − | − |
| Staphylococcus aureus | ATCC 6538 | − | − |

TABLE 1-continued

Results using a panel of reference strains and isolates representing clinically relevant and phylogenetically related bacterium and yeast species.

| Species | Strain ID | Bant23S03/Flu Bant23S03BLK | Bant23S02/ Flu |
|---|---|---|---|

[a]type strain

Each of the single PNA oligomer (Bant23SO2/Flu) or a mixture (set) of PNA oligomers (Bant23S03/Flu & Bant23S03/BLK) was tested on a panel of reference strains representing twelve Bacillus species, including all other type strains of the B. cereus complex, i.e. B. cereus, B. thuringiensis, B. mycoides, B. weihenstephaniensis and B. pseudomycoides, as well as three other bacterium species commonly found in blood culture. Results are summarized in Table 1.

Bant2302/Flu showed 100% sensitivity and 100% specificity whereas Bant23S03/Flu:Bant23S03/BLK showed 100% sensitivity and 71% specificity. With reference to the images shown in FIGS. 1A and 1B, which are examples of the results obtained, the Bacillus anthracis (FIG. 1A) are stained green because of the presence of the fluorescein labeled PNA oligomer probe whereas the B. pseudomycoides do not stain green under the same conditions and are faint red in color; likely due to autofluorescence.

Studies including additional reference strains and isolates from various clinical specimens, including blood cultures, were performed in parallel hybridization reactions with the two probes, such that identification of B. anthracis was based on positive reactions with both probes. These data are summarized in Table 2 and showed 100% (2/2) sensitivity and 93.3% (42/45) specificity.

TABLE 2

Results of panel of reference strains and clinical isolates of various Bacillus species.

| | Result | |
|---|---|---|
| Species (n) | Positive (n) | Negative (n) |
| Bacillus anthracis (2) | 2 | 0 |
| Bacillus cereus (7) | 1 | 6 |
| Bacillus thuringiensis subspp (23) | 2 | 21 |
| Bacillus spp (non-B. anthracis) (15) | 0 | 15 |

EQUIVALENTS

While this invention has been particularly shown and described with references to preferred embodiments thereof, it will be understood by those of ordinary skill in the art that various changes in form and details may be made therein without departing from the spirit and scope of the invention as defined by the appended claims. Those skilled in the art will be able to ascertain, using no more than routine experimentation, many equivalents to the specific embodiments of the invention described herein.

We claim:

1. A PNA oligomer comprising a probing nucleobase sequence that is at least ninety percent homologous to a nucleobase sequence, or its complement, selected from the group consisting of: CCA-SSG-GTA-TCD-DTC (Seq. ID No. 1) and TTC-AAA-GGC-TCC-CGC (Seq. ID No. 2).

2. The PNA oligomer of claim 1, wherein the probing nucleobase sequence is one hundred percent homologous to one of Seq. ID No. 1 or Seq. ID No. 2, or their complements.

3. The PNA oligomer of claim 1, wherein the oligomer is unlabeled.

4. The PNA oligomer of claim 1, wherein the oligomer is labeled with at least one detectable moiety.

5. The PNA oligomer of claim 4, wherein the detectable moiety or moieties are each independently selected from the group consisting of: a dextran conjugate, a branched nucleic acid detection system, a chromophore, a fluorophore, a spin label, a radioisotope, an enzyme, a hapten, an acridinium ester and a chemiluminescent compound.

6. The PNA oligomer of claim 5, wherein the enzyme is selected from the group consisting of alkaline phosphatase, soybean peroxidase, horseradish peroxidase, ribonuclease and protease.

7. The PNA oligomer of claim 5, wherein the hapten is selected from the group consisting of fluorescein, biotin, 2,4-dinitrophenyl and digoxigenin.

8. The PNA oligomer of claim 1, wherein the oligomer is labeled with at least two independently detectable moieties.

9. The PNA oligomer of claim 8, wherein the two or more independently detectable moieties are independently detectable fluorophores.

10. The PNA oligomer of claim 1, wherein the oligomer comprises a non-fluorescent quencher moiety.

11. The PNA oligomer of claim 1, wherein the oligomer comprises an energy transfer set of labels.

12. The PNA oligomer of claim 1, wherein the oligomer is support bound.

13. A PNA oligomer that:
   a) comprises one or more non-natural nucleobases comprising a sequence that is at least ninety percent homologous to a nucleobase sequence, or its complement, selected from the group consisting of: CCA-SSG-GTA-TCD-DTC (Seq. ID No. 1) and TTC-AAA-GGC-TCC-CGC (Seq. ID No. 2);

b) does not substantially intra or inter molecularly self-hybridize; and c) sequence-specifically hybridizes to a region of the nucleic acid of *Bacillus anthracis*.

14. The PNA oligomer of claim 13, wherein the non-natural nucleobases are each independently selected from the group consisting of: 2,6-diaminopurine, 2-thiouracil and 2-thiothymine.

15. The PNA oligomer of claim 13, wherein the oligomer is unlabeled.

16. The PNA oligomer of claim 13, wherein the oligomer is labeled with at least one detectable moiety.

17. The PNA oligomer of claim 16, wherein the detectable moiety or moieties are each independently selected from the group consisting of: a dextran conjugate, a branched nucleic acid detection system, a chromophore, a fluorophore, a spin label, a radioisotope, an enzyme, a hapten, an acridinium ester and a chemiluminescent compound.

18. The PNA oligomer of claim 17, wherein the enzyme is selected from the group consisting of alkaline phosphatase, soybean peroxidase, horseradish peroxidase, ribonuclease and protease.

19. The PNA oligomer of claim 17, wherein the hapten is selected from the group consisting of fluorescein, biotin, 2,4-dinitrophenyl and digoxigenin.

20. The PNA oligomer of claim 13, wherein the oligomer is labeled with at least two independently detectable moieties.

21. The PNA oligomer of claim 20, wherein the two or more independently detectable moieties are independently detectable fluorophores.

22. The PNA oligomer of claim 13, wherein the oligomer comprises a non-fluorescent quencher moiety.

23. The PNA oligomer of claim 13, wherein the oligomer comprises an energy transfer set of labels.

24. The PNA oligomer of claim 13, wherein the oligomer is support bound.

25. An oligomer set comprising two or more oligomers, at least one of which is a PNA oligomer comprising a probing nucleobase sequence that is at least ninety percent homologous to a nucleobase sequence, or its complement, selected from the group consisting of: CCA-SSG-GTA-TCD-DTC (Seq. ID No. 1) and TTC-AAA-GGC-TCC-CGC (Seq. ID No. 2).

26. A method comprising: a) contacting a sample, under suitable hybridization conditions, with at least one PNA oligomer comprising a probing nucleobase sequence that is at least ninety percent homologous to a nucleobase sequence, or its complement, selected from the group consisting of: CCA-SSG-GTA-TCD-DTC (Seq. ID No. 1) and TTC-AAA-GGC-TCC-CGC (Seq. ID No. 2); and b) detecting, identify and/or quantitating hybridization of the probing nucleobase sequence of a PNA oligomer to a target sequence within the nucleic acid of *Bacillus anthracis* and correlating the result with the presence, absence and/or quantity of *Bacillus anthracis* in the sample.

27. A kit comprising:
a) one or more PNA oligomers comprising a probing nucleobase sequence that is at least ninety percent homologous to a nucleobase sequence, or its complement, selected from the group consisting of: CCA-SSG-GTA-TCD-DTC (Seq. ID No. 1), TTC-AAA-GGC-TCC-CGC (Seq. ID No. 2) and TTC-AAT-GGC-TCC-CGC (Seq. ID No. 3); and b) other reagents, instructions or compositions useful in performing an assay suitable for determining the presence, absence and/or quantity of the nucleic acid of *Bacillus anthracis* in a sample.

* * * * *